US00PP23069P2

(12) United States Plant Patent
Sawada

(10) Patent No.: US PP23,069 P2
(45) Date of Patent: Sep. 25, 2012

(54) ***MAYTENUS* PLANT NAMED 'HEART NO KI'**

(50) Latin Name: *Maytenus diversifolia*
Varietal Denomination: Heart No Ki

(75) Inventor: Kotaro Sawada, Tokoname (JP)

(73) Assignee: Sawada Noen, Tokoname-shi, Aichi (JP)

( * ) Notice: Subject to any disclaimer, the term of this patent is extended or adjusted under 35 U.S.C. 154(b) by 63 days.

(21) Appl. No.: 12/930,159

(22) Filed: Dec. 29, 2010

(51) Int. Cl.
*A01H 5/00* (2006.01)

(52) U.S. Cl. ..... Plt./226

(58) Field of Classification Search ..... Plt./226, Plt./216

See application file for complete search history.

*Primary Examiner* — June Hwu

(74) *Attorney, Agent, or Firm* — C. A. Whealy

(57) ABSTRACT

A new and distinct cultivar of *Maytenus* plant named 'Heart No Ki', characterized by its upright and outwardly spreading plant habit; vigorous growth habit; freely branching habit; dark green-colored leaves; freely flowering habit; and attractive greyed purple-colored fruits.

2 Drawing Sheets

Botanical designation: *Maytenus diversifolia.*
Cultivar denomination: 'Heart No Ki'.

BACKGROUND OF THE INVENTION

The present invention relates to a new and distinct cultivar of *Maytenus* plant, botanically known as *Maytenus diversifolia* and hereinafter referred to by the name 'Heart No Ki'.

The new *Maytenus* plant is a naturally-occurring whole plant mutation of an unnamed selection of *Maytenus diversifolia*, not patented. The new *Maytenus* plant was discovered and selected by the Inventor as a single flowering plant within a population of plants of the parent selection in a controlled greenhouse environment in Tokoname-shi, Aichi-prefecture, Japan in April, 2006.

Asexual reproduction of the new *Maytenus* plant by terminal cuttings in a controlled environment in Tokoname-shi, Aichi-prefecture, Japan since April, 2006, has shown that the unique features of this new *Maytenus* plant are stable and reproduced true to type in successive generations.

SUMMARY OF THE INVENTION

Plants of the new *Maytenus* have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Heart No Ki'. These characteristics in combination distinguish 'Heart No Ki' as a new and distinct *Maytenus* plant:

1. Upright and outwardly spreading plant habit.
2. Vigorous growth habit.
3. Freely branching habit.
4. Dark green-colored leaves.
5. Freely flowering habit.
6. Attractive greyed purple-colored fruits.

Plants of the new *Maytenus* can be compared to plants of the parent selection. Plants of the new *Maytenus* differ primarily from plants of the parent selection in the following characteristics:

1. Plants of the new *Maytenus* are narrower and more upright than plants of the parent selection.
2. Plants of the new *Maytenus* have larger fruits than plants of the parent selection.

Plants of the new *Maytenus* can also be compared to plants of other (non-parental) unnamed selections of *Maytenus diversifolia*, not patented. Plants of the new *Maytenus* and other unnamed selections of *Maytenus diversifolia* differ primarily in plant form as plants of the new *Maytenus* are more upright. In addition, plants of the new *Maytenus* have larger fruits than plants of other unnamed selections of *Maytenus diversifolia.*

BRIEF DESCRIPTION OF THE PHOTOGRAPHS

The accompanying colored photographs illustrate the overall appearance of the new *Maytenus* plant showing the colors as true as it is reasonably possible to obtain in colored reproductions of this type. Colors in the photographs may differ slightly from the color values cited in the detailed botanical description which accurately describe the colors of the new *Maytenus* plant.

The photograph on the first sheet comprises a side perspective view of a typical flowering plant of 'Heart No Ki' grown in a container.

The photograph on the second sheet is a close-up view of a typical flowering and fruiting branch of 'Heart No Ki'.

DETAILED BOTANICAL DESCRIPTION

The aforementioned photographs and following observations, measurements and values describe plants grown during the spring and early summer in 13.5-cm containers in a polyethylene-covered greenhouse in Tokoname-shi, Aichi-prefecture, Japan and under commercial practices. During the production of the plants, day temperatures ranged from 5° C. to 30° C. and night temperatures ranged from −3° C. to 25° C. Plants were two years old when the photographs and description were taken. In the following description, color references are made to The Royal Horticultural Society Colour Chart, 2001 Edition, except where general terms of ordinary dictionary significance are used.

Botanical classification: *Maytenus diversifolia* 'Heart No Ki'.

Parentage: Naturally-occurring whole plant mutation of an unnamed selection of *Maytenus diversifolia*, not patented.

Propagation:

*Type*.—By cuttings.

*Time to produce a rooted young plant, summer*.—About one to two months at soil temperatures of 25° C. to 30° C.

*Time to produce a rooted young plant, winter*.—About two to three months at soil temperatures of 10° C. to 20° C.

*Root description*.—Medium in thickness, fibrous.

*Rooting habit*.—Sparse.

Plant description:

*Plant and growth habit*.—Evergreen shrub; upright and outwardly spreading plant habit; freely branching habit with numerous lateral branches developing per plant; pinching enhances lateral branch development; vigorous growth habit.

*Plant height*.—About 60 cm.

*Plant diameter*.—About 30 cm.

Lateral branch description:

*Length*.—About 43 cm.

*Diameter*.—About 1 mm.

*Internode length*.—About 1.5 cm.

*Strength*.—Strong.

*Aspect*.—Upright to outwardly.

*Texture*.—Smooth, glabrous.

*Color*.—Close to 165A.

Foliage description:

*Arrangement*.—Whorled, simple.

*Length*.—About 2.2 cm.

*Width*.—About 1.4 cm.

*Shape*.—Obovate.

*Apex*.—Acute.

*Base*.—Attenuate.

*Margin*.—Crenate.

*Texture, upper and lower surfaces*.—Smooth, glabrous.

*Venation pattern*.—Pinnate; reticulate.

*Color*.—Developing leaves, upper surface: Close to 137C. Developing leaves, lower surface: Close to 137D. Fully expanded leaves, upper surface: Close to 139A; venation, close to 138B. Fully expanded leaves, lower surface: Close to 137D; venation, close to 138A.

*Petioles*.—Length: About 1.5 mm. Diameter: About 0.8 mm. Texture, upper and lower surfaces: Smooth, glabrous. Color, upper and lower surfaces: Close to 138B.

Flower description:

*Flower arrangement and habit*.—Single star-shaped flowers arranged on axillary racemes; freely flowering habit with usually about 120 flowers developing per lateral branch; flowers face upright.

*Fragrance*.—None detected.

*Natural flowering season*.—Plants of the new *Maytenus* flower naturally from May until November in Japan.

*Flower longevity*.—Individual flowers last about two weeks on the plant; flowers not persistent.

*Flower diameter*.—About 5 mm.

*Flower length* (*depth*).—About 1.3 mm.

*Flower bud*.—Shape: Globular. Length: About 1 mm. Diameter: About 0.5 mm. Color: Close to 155A.

*Petals*.—Quantity/arrangement: Five petals arranged in a single whorl. Length: About 1.2 mm Width: About 0.8 mm. Shape: Deltoid. Apex: Acute. Margin: Entire. Texture, upper and lower surfaces: Smooth, glabrous. Color: When opening, upper and lower surfaces: Close to 155A. Fully opened, upper and lower surfaces: Close to 155A.

*Sepals*.—None observed.

*Peduncles*.—Length: About 5 mm. Diameter: Less than 1 mm. Strength: Strong. Texture: Smooth, glabrous.

*Reproductive organs*.—Stamens: Quantity/arrangement: Five per flower. Stamen length: Less than 1 mm. Pistils: Quantity: One per flower. Pistil length: Less than 1 mm. Fruits: Quantity per lateral branch: About 70. Length: About 7 mm. Diameter: About 7 mm. Shape: Cordate. Texture: Smooth, glabrous. Color: Close to 184B. Seeds: Quantity per fruit: About one to four. Length: About 3.6 mm. Diameter: About 2.4 mm. Texture: Smooth, glabrous. Color: Close to 173B.

Temperature tolerance: Plants of the new *Maytenus* have been observed to tolerate temperatures ranging from about −5° C. to about 40° C.

Pathogen/pest resistance: Plants of the new *Maytenus* have not been observed to be resistant to pathogens and pests common to *Maytenus* plants.

It is claimed:

1. A new and distinct *Maytenus* plant named 'Heart No Ki' as illustrated and described.

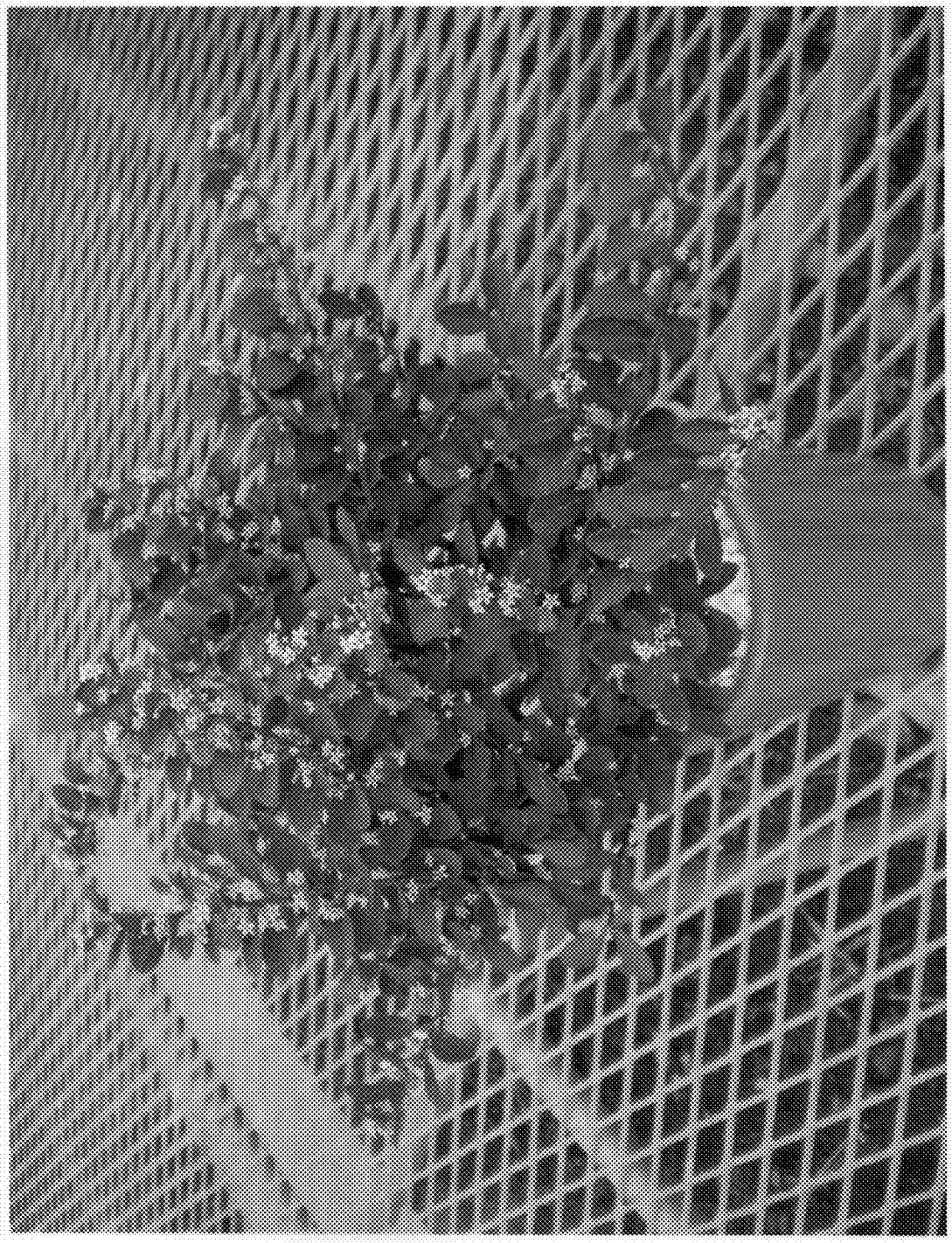

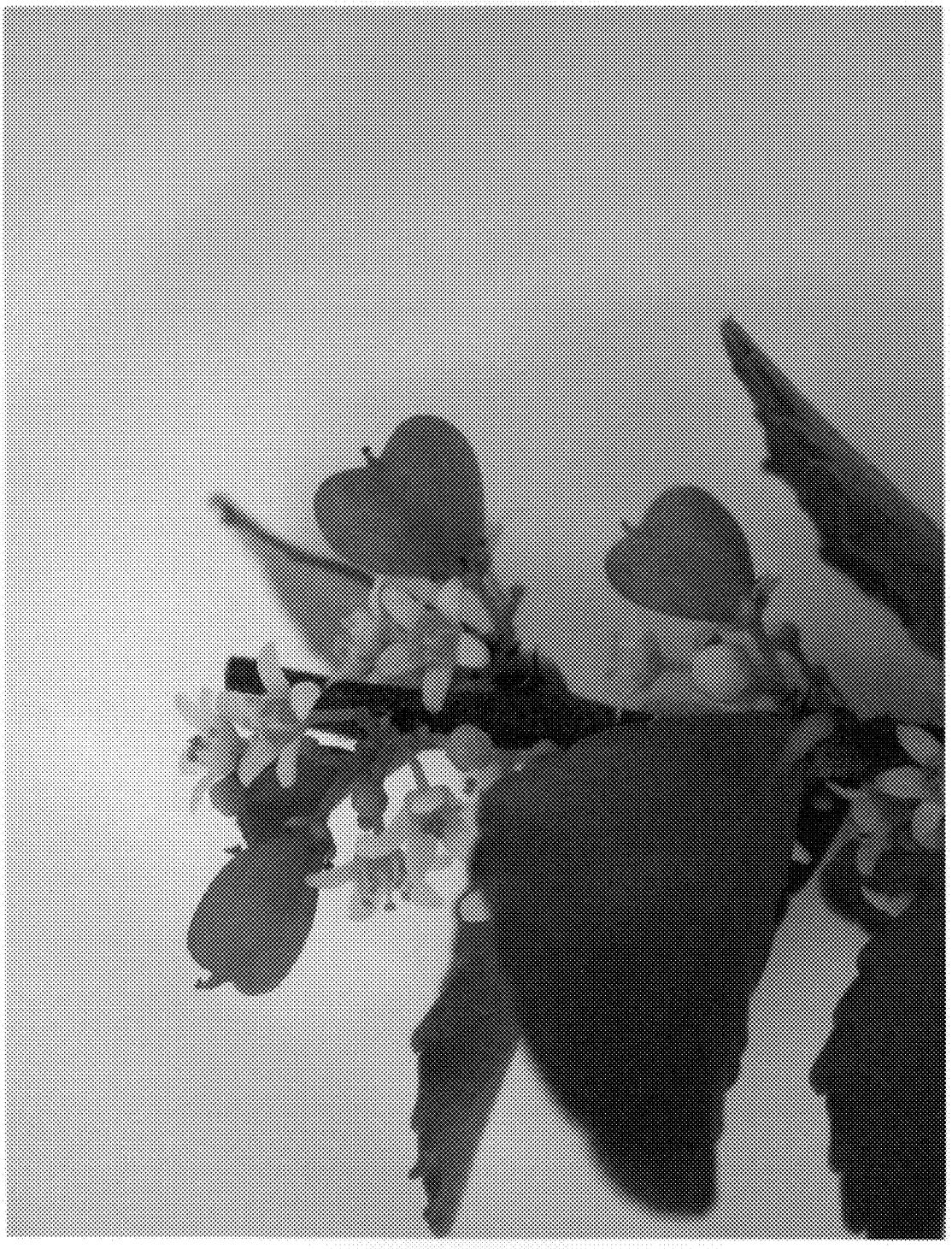

* * * * *